(12) United States Patent
Mikael

(10) Patent No.: US 7,405,578 B2
(45) Date of Patent: Jul. 29, 2008

(54) DEVICE FOR MONITORING THE CONTACT INTEGRITY OF A JOINT

(76) Inventor: Dautrey Mikael, 18, Rue des Fougeres, Perros-Guirec (FR) 22 700

( * ) Notice: Subject to any disclaimer, the term of this patent is extended or adjusted under 35 U.S.C. 154(b) by 0 days.

(21) Appl. No.: 10/543,208

(22) PCT Filed: Jan. 6, 2004

(86) PCT No.: PCT/FR2004/000008

§ 371 (c)(1),
(2), (4) Date: Jul. 22, 2005

(87) PCT Pub. No.: WO2004/079353

PCT Pub. Date: Sep. 16, 2004

(65) Prior Publication Data

US 2006/0186902 A1    Aug. 24, 2006

(30) Foreign Application Priority Data

Jan. 29, 2003   (FR) .................................. 03 00955

(51) Int. Cl.
*G01R 27/08*  (2006.01)
*G01R 31/08*  (2006.01)
*G01R 31/02*  (2006.01)

(52) U.S. Cl. ........................ 324/697; 324/691; 324/525; 324/756; 324/757

(58) Field of Classification Search ................ 324/525, 324/697, 691, 756, 757
See application file for complete search history.

(56) References Cited

U.S. PATENT DOCUMENTS

| | | | | |
|---|---|---|---|---|
| 4,503,710 | A | 3/1985 | Oertle et al. | 73/763 |
| 5,969,532 | A | 10/1999 | Usui et al. | 324/557 |
| 6,906,541 | B2 | 6/2005 | Kimura | 324/754 |
| 2006/0012375 | A1 | 1/2006 | Kelsey et al. | 324/525 |

*Primary Examiner*—Vincent Q. Nguyen
*Assistant Examiner*—Amy He (57) ABSTRACT

The invention relates to a device that can be used to monitor the contact integrity of a joint that is of an impervious contact surface between two parts (4 and 5) including a set of conductive patterns (8) which are distributed over the two contact surfaces (1 and 2) and which are separated by insulating zones (9). When the aforementioned two parts (4 and 5) are brought into contact, the conductive patterns (8) also come into contact and form a conductor between the two measuring points (6 and 7), which is made by positioning the resistances of the patterns (8) in series. Any local change in the contact between the patterns causes the intensity and voltage between points (6) and (7) to vary and is measured with a measuring device (22). The invention is particularly suitable for the detection of an intrusion or a leak between two sealed contact parts.

9 Claims, 12 Drawing Sheets

DEVICE FOR MONITORING THE CONTACT INTEGRITY OF A JOINT

BACKGROUND OF THE INVENTION

1. Technical Field

The present invention relates to a device for measuring in a continuous way the modification of the physical contact between two curvilinear contact surfaces on the basis of a measurement of resistance.

By curvilinear, one means a surface that is built on a direct curve and sections of this direct curve. A section is a line segment, rectilinear or not, which is definite for each point of the direct curve. The sections form a set of rectilinear lines or not that cross the direct curve but do not cross each other. The direct curve and the set of sections define a surface. The surface thus defined can be plane or not. We call edges of the contact surface the set of the endpoints of the sections. The curvilinear surface thus has two edges. It also has two ends, confused or not, which are the two sections located at the ends of the direct curve and are called ends of the surface. We call joint a curvilinear contact surface between two elements.

2. Description of Related Art

Detection of either leak or matter intrusion is traditionally achieved with the help of external sensors detecting the abnormal presence of the matter following its passage between two contact elements that should carry out a tight border between two zones. These sensors can be sensors measuring the pressure of a fluid, or sensors allowing the detection of a chemical compound, or sensors allowing the detection of matter presence or any other type of sensors according to the application. The sealing degradation is then detected when the matter passage between the two zones took place, i.e. after the break of sealing, which can be saw as a break of the contact surface integrity forming a way between both edges of the surface. The extent of the degradation is then estimated from the quantity of matter that crossed from one zone to the other by its path.

The monitoring of sealing of tight doors and tight trap doors is also usually carried out by measurement of difference in pressure, which do not make is possible to check the correct positioning of the seal of the door or the trap door for example in U.S. Pat. Nos. 4,202,201 issued May 13, 1980, or 5,404,747 issued Apr. 11, 1995.

Another technique for detecting leaks consists in measuring the pressure on the sealing membrane. The leak is thus detected by a pressure drop on the membrane surface following the transition from a hydrostatic mode of pressure to a dynamic mode of pressure. This technique does not make it possible either to detect the surface deterioration before the leak occurs. A possible pressure measuring device system for this application is disclosed in the U.S. Pat. No. 4,446,424 issued May 1, 1984.

Another technique for detecting leaks, disclosed in the G.B. Pat. 1,535,047 issued Dec. 6, 1978, is based on the detection of the emergence of a flow of electricity following the passage of a conductive liquid between the two contact surfaces. This method, of all-or-nothing-type, does not make it possible to measure the extent of the seal degradation. Moreover, it can only be used to detect the intrusion of conductive matter between the two contact surfaces. This method does not allow to detect a seal deterioration by the intrusion of insulating matter.

BRIEF SUMMARY OF THE INVENTION

The present invention makes it possible to remedy these drawbacks, while monitoring the contact integrity between two parts in contact according to a curvilinear surface thanks to the measurement of a resistance. It thus makes it possible to detect and measure the partial separation of the contact in any point of the contact surface before the leak or the intrusion and thus to foresee and prevent this event.

Each of the two contact surfaces is paved with patterns separated from each other by insulating zones e.g. zones less conductive than the patterns. The patterns can be either surface patterns or some thick patterns incorporated in the material forming the joint and showing through its surface. The present invention does not impose any restriction on the distribution in the contact parts volume of the matter making up the pattern. For each pattern, only the part showing through the contact zone has to be defined.

By conduction, one understands conduction in the broad sense, i.e. response in intensity in relation to an electrical powering, the tension being continuous or variable over time.

The insulating zone is a zone whose conductivity can take a determined value ranging between a null or quasi-null (close to perfect insulator) conductivity and a low conductivity relative to that of the patterns.

The electric characteristics of the patterns and insulating zones are not necessarily homogeneous either in volume or on contact surface.

The succession of patterns and insulating zones can thus be obtained by continuous variation of the electric characteristics of a material.

One defines a conductive line as a line joining the two ends of the curvilinear surface and homotopic to its direct line. The paving of each of the two contact surfaces is designed in such a way that their superposition forms and unbroken conductive surface according to a conductive line of the curvilinear surface, i.e. so that it is possible to draw between the two ends of the curvilinear surface a conductive line contained in the surface formed by the assembly of the patterns of the two surfaces. We call this line, a chain of conductors formed by the superimposition of the patterns.

The patterns are made so that all the time the two surfaces are in contact, each pattern of one surface is in contact with at least two consecutive patterns along the conduction line of the other surface, and each pattern of the latter surface is in contact with at least two consecutive patterns of the former surface. When the two surfaces are brought into contact, the patterns also come into contact and form a chain of conductors according to the conduction line of the patterns between the two ends of the curvilinear surface, patterns are arranged so that the chain of conductors thus made up is a resistive dipole made up of the resistances of the patterns connected in series. A device for measuring the intensity and the voltage between the two ends of the chain of conductors makes it possible to measure the contact quality between the two surfaces and its variations as time goes. In the event of a detachment having an effect on the conductive surface, a modification of intensity and voltage is measured between both ends. In the event of a leak or an intrusion according to a path joining the two edges of the contact surface through the conduction surface, a resistance increase or even a conduction break between the two ends is detected. As patterns are positioned in series on the conduction line, the resistance variation of the conductor from end to end equals the resistance variation of one of the patterns during a contact variation between both surfaces. The claimed device also works when each pattern is in contact with more than two patterns of the opposite surface. In that case, the resistance from end to end is made up of resistances in parallel and in series. In every case, the resistance variation is the result of the localized variation of the contact between both parts.

BRIEF DESCRIPTION OF THE SEVERAL VIEWS OF THE DRAWINGS

FIG. (1) shows a cross-section of the general problems solved by the invention. Two elements (4 and 5) make a tight border between two zones (12) and (13). These two elements are in contact through a curvilinear contact surface. This curvilinear surface corresponds to two physical surfaces, contact surface (1) of element (4) and contact surface (2) of element (5).

FIG. (2) is a side view. (3) is the contact zone between contact surfaces (1) of part (4) and (2) of part (5). (3) is thus the joint between the two parts, on a longitudinal view. Device (22) measures the resistance between the two connection points (6 and 7). According to the connection chosen, (6 and 7) can be connected to the same contact surface, (1) for example, or to each surface, (6) being connected to (1) and (7) to (2).

FIG. (3) shows a cross-section of each contact surface (1 and 2). The claimed device comprises patterns (8) that are more conductive than the insulating zone (9).

FIG. (4) shows the superposition of two surfaces (1 and 2), seen on top. (23) is what we call the chain of conductors, which connects the connection points (6 and 7) of the patterns (8).

FIG. (5) is a view similar to FIG. (4). The conduction surface, intersection of patterns (1 and 2), is represented in grey tint (10). You observe that the zone (11), which is a contact between a pattern of (1) and a pattern of (2), is however not included in the conductor between (6) and (7), what creates a potential zone of shade which can be reduced by the use of multiple connection points as further presented.

FIG. (6) shows a cross-section of the claimed device with a uniform contact between the two pieces (4) and (5) along the whole surface.

FIG. (7) is a view similar to FIG. (6), but with a detachment of surface in (14). The detachment of surface caused a break of conduction between (6) and (7).

FIG. (8) is a view like FIG. (3), but in case the two connection points (6 and 7) are not on the same surface. Connection point (6) is on surface (1) while connection point (7) is on surface (2).

FIG. (9) is a view like FIG. (4), but in case the two connection points (6 and 7) are not on the same surface.

FIG. (1) is a view like FIG. (5), but in case the two connection points (6 and 7) are not on the same surface.

FIG. (11) is a view like FIG. (6), but in case the two connection points (6 and 7) are not on the same surface.

FIG. (12) is a view like FIG. (7), but in case the two connection points (6 and 7) are not on the same surface.

FIG. (13) shows two conduction lines with staggered patterns between the two lines, that increases the device sensitivity. The connection points (15 and 16) of the second line have been arranged on the other contact surface. It is possible to arrange them equally either on one or the other surface. It is also possible to thus build any number of conduction lines.

FIG. (14) completes FIG. (13) by showing the juxtaposition of the patterns. The use of several conduction lines makes it possible to pave the contact surface in a optimal way with patterns.

FIG. (15) shows the device use in the case of a circular seal, which can be, more generally, a seal in closed curve. The conductor is obtained by making coincide two insulating zones (17) of the contact surfaces (1 and 2) when (1 and 2) are brought into contact. The insulating zones of one of the two contact surfaces are overlapped by a pattern of the other surface. The contact surface is also connected to many connection points, (6 and 7), that are positioned at the end of the chain of conductors, and (18, 19 and 20) that are distributed on the chain of conductors. This configuration makes it possible to measure the resistance between the various connection points to locate the zones of possible detachment of the contact by successive measurements between the two same points.

FIG. (16) shows a specific pattern shape, identical for both surfaces (1 and 2). This shape guarantees a contact between each pattern of one of the contact surfaces with at least two patterns of the opposite surface, whatever the relative position of the two contact surfaces.

FIG. (17) shows another set of patterns, patterns of surface (1) being perpendicular to patterns of surface (2). This configuration offers the same characteristics as those of FIG. (16), that is to say a contact of each pattern with at least two patterns of the opposite surface whatever the position, and an optimisation of the cover of the contact surface.

FIG. (18) shows a variant of the device in which the two surfaces (1 and 2) are not any more in contact but are linked together with a seal (21) made up of a conductive element according to parallel lines or not, conductive fibers for example, and which puts together both contact surfaces (1 and 2). These conductive lines can be perpendicular to the two contact surfaces, thus connecting points which would be in matter contact in the absence of (21). They can also be directed differently. This kind of material can be obtained by embedding conducting fibers in insulating material such as rubber or any other process.

FIG. (19) is a view similar to FIG. (18) where the connection points (6 and 7) are not positioned on the same surface.

DETAILED DESCRIPTION OF THE INVENTION

We call conduction surface, the surface defined by the intersection of the patterns of surfaces (1 and 2) and we call insulating surface, the complementary surface to the conduction surface of the curvilinear contact surface.

Figure 1:
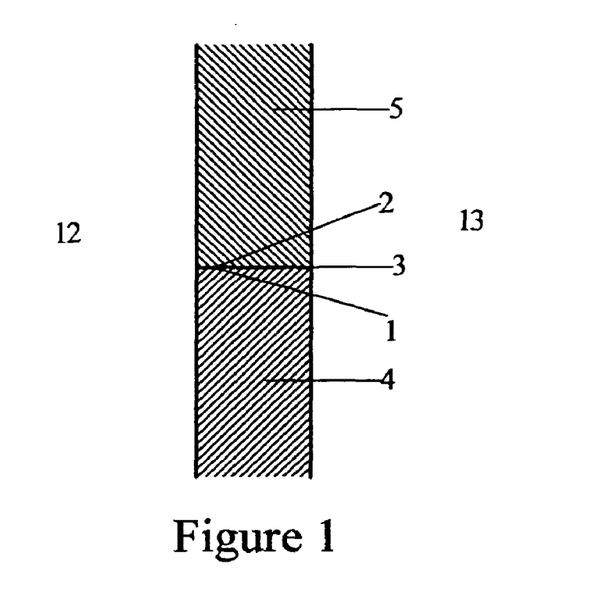
Figure 2:
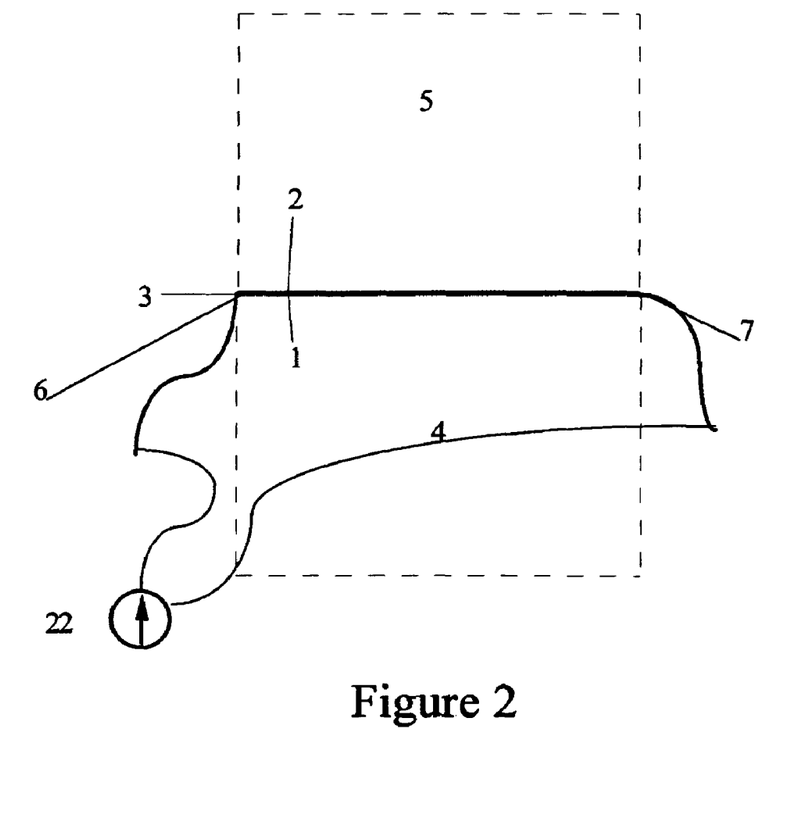
Figure 3:
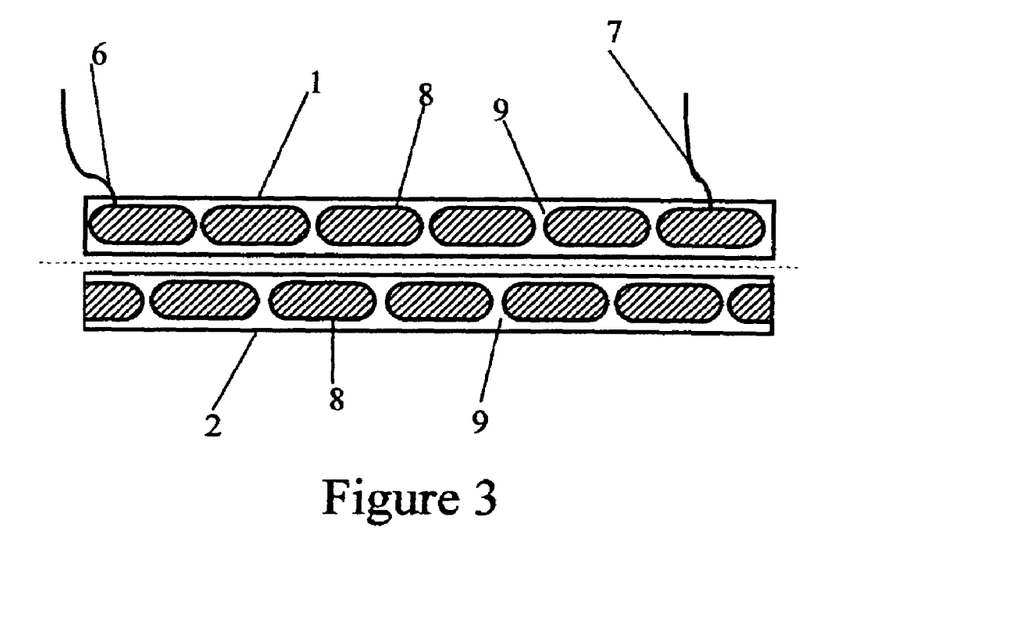
Figure 4:
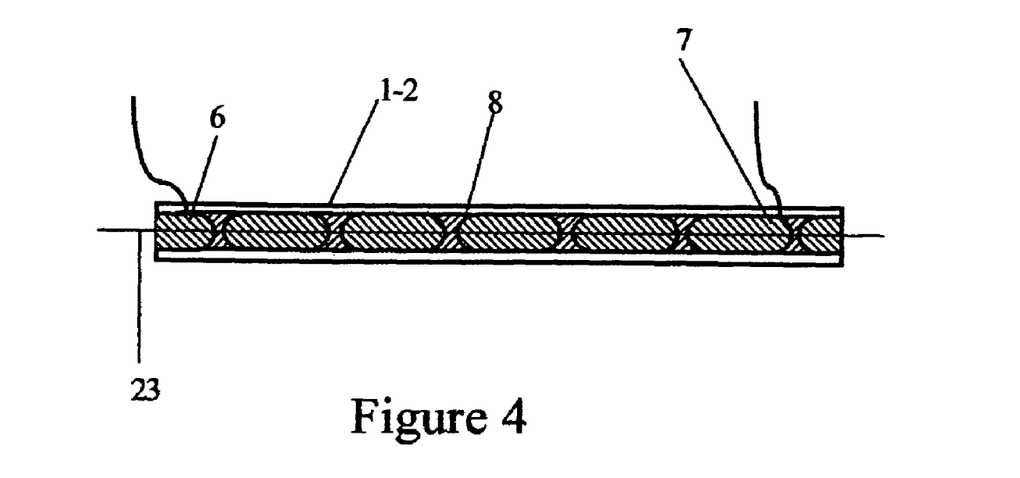
Figure 5:
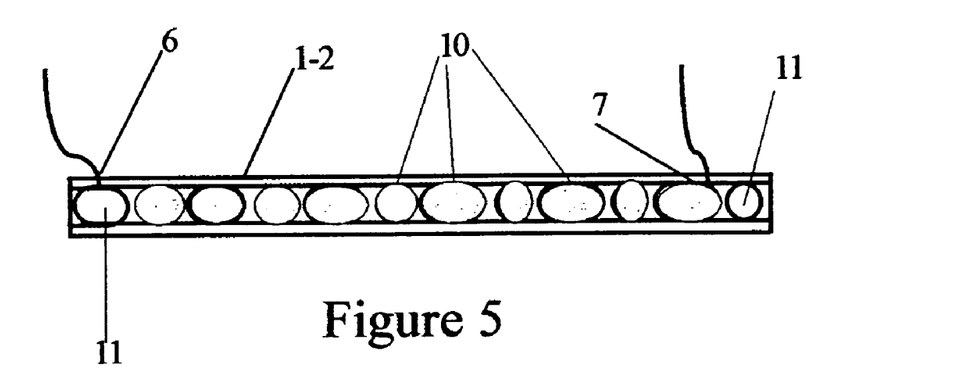
Figure 6:
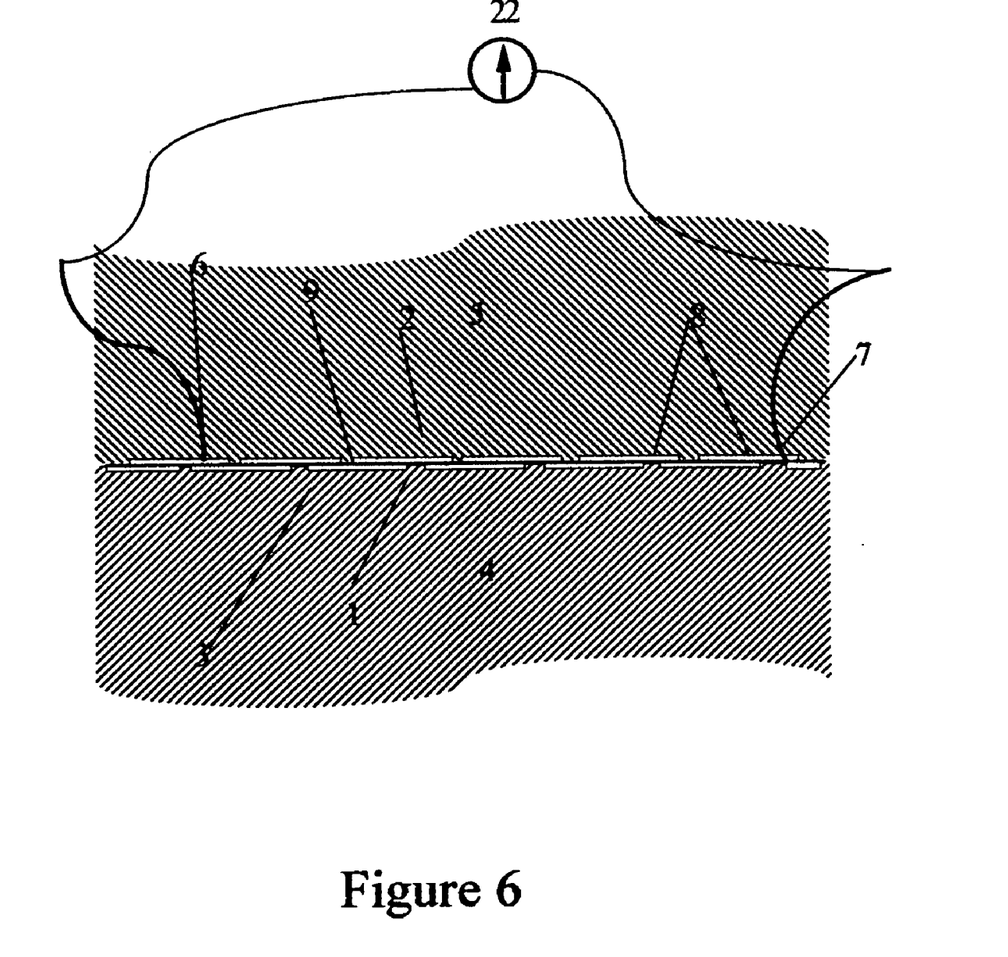
Figure 7:
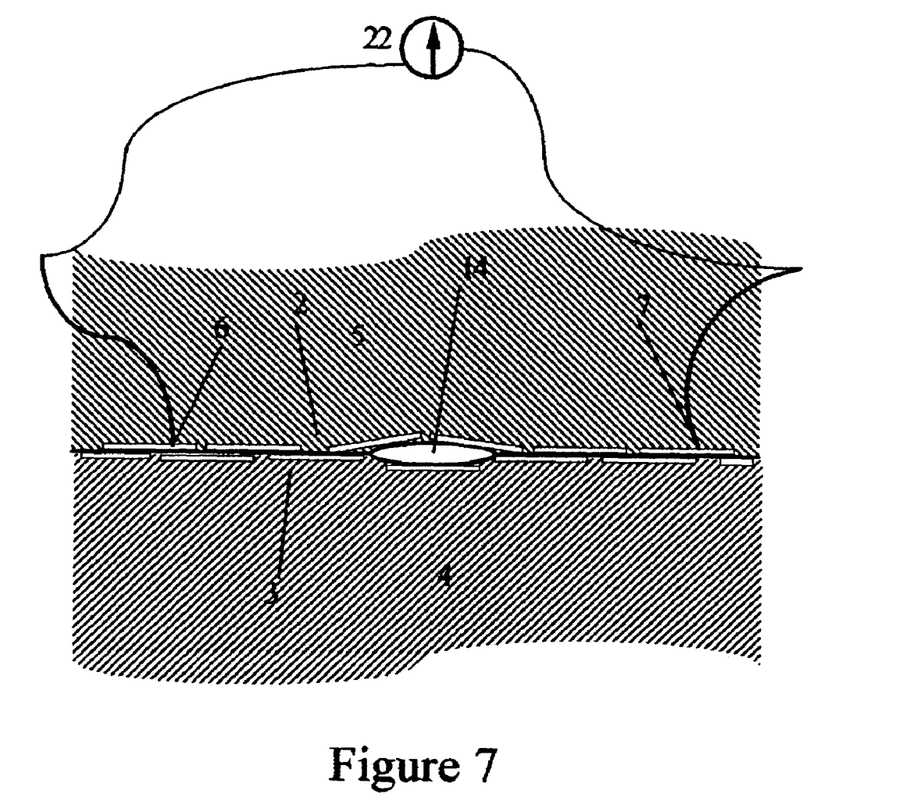
Figure 8:
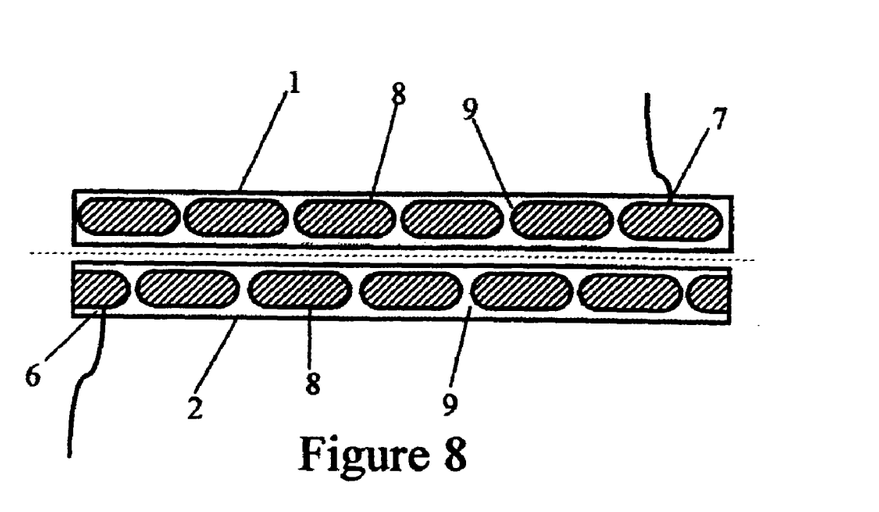
Figure 9:
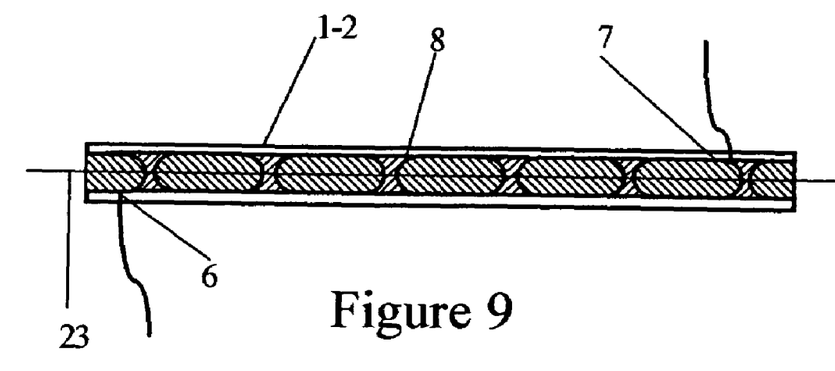
Figure 10:
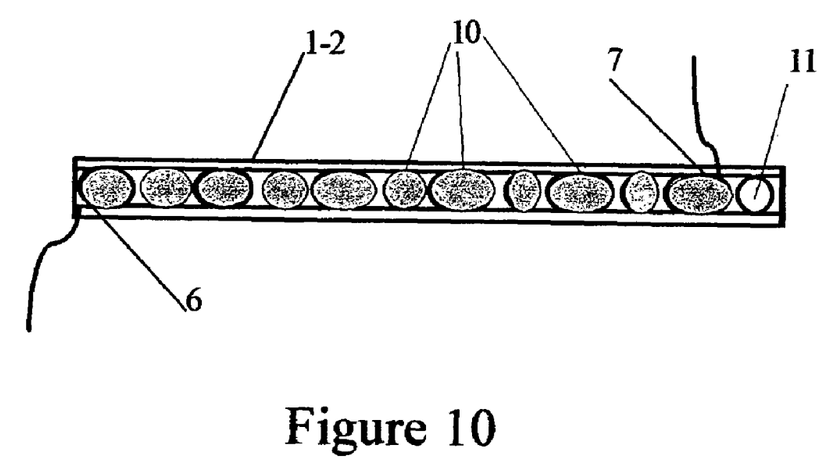
Figure 11:
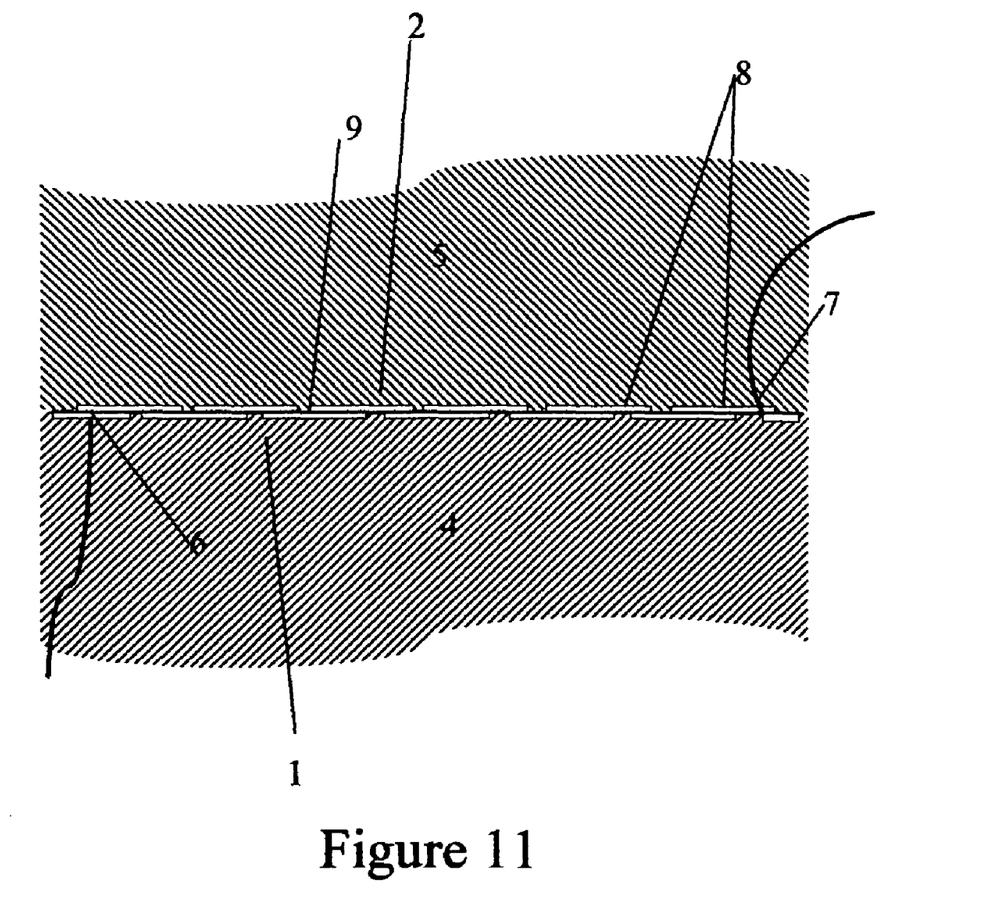
Figure 12:
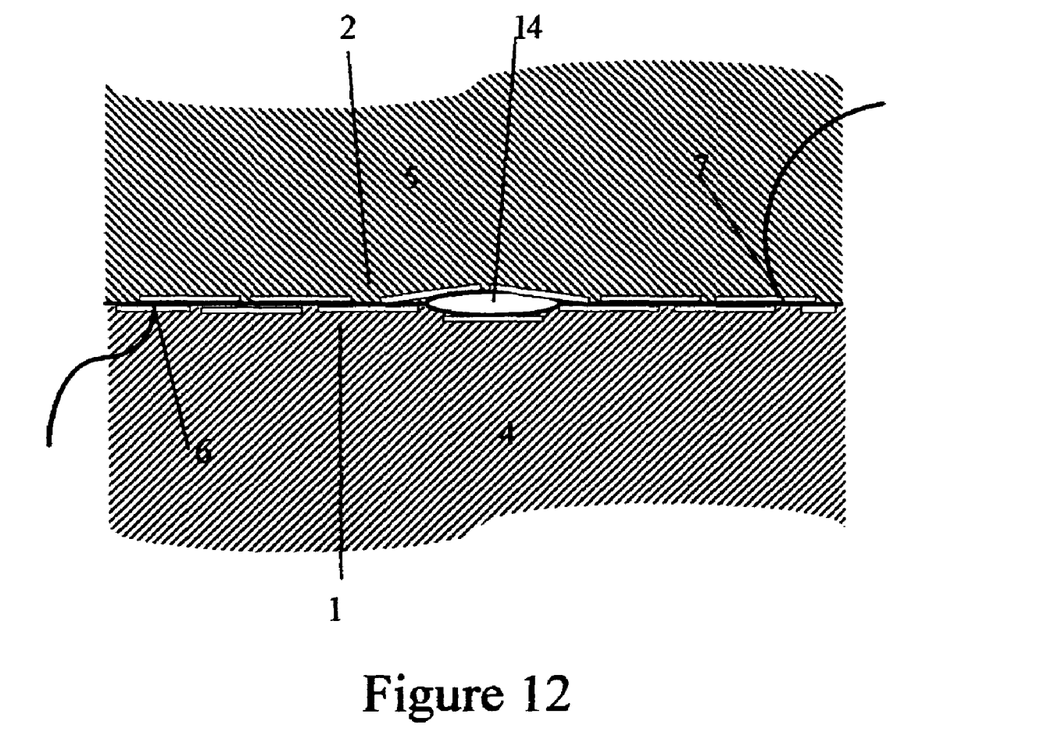
Figure 13:
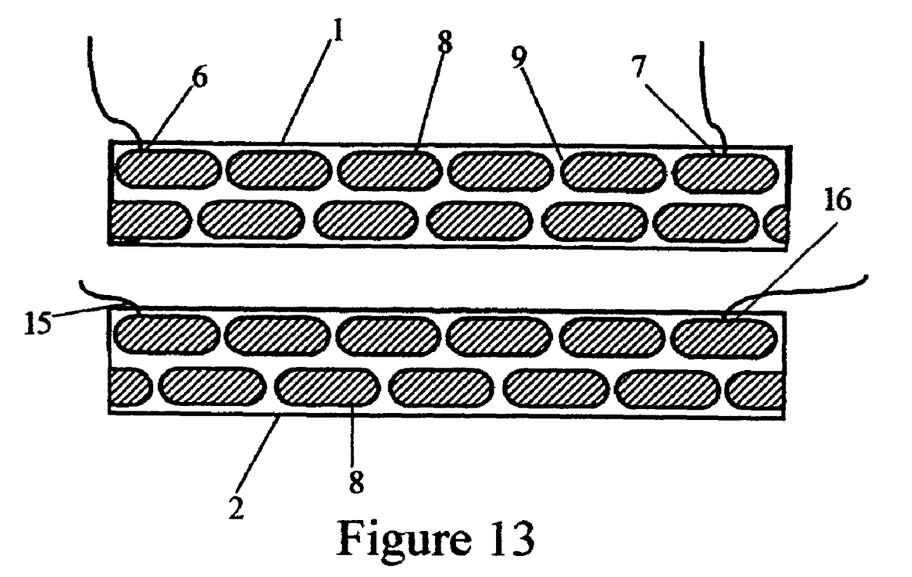
Figure 14:
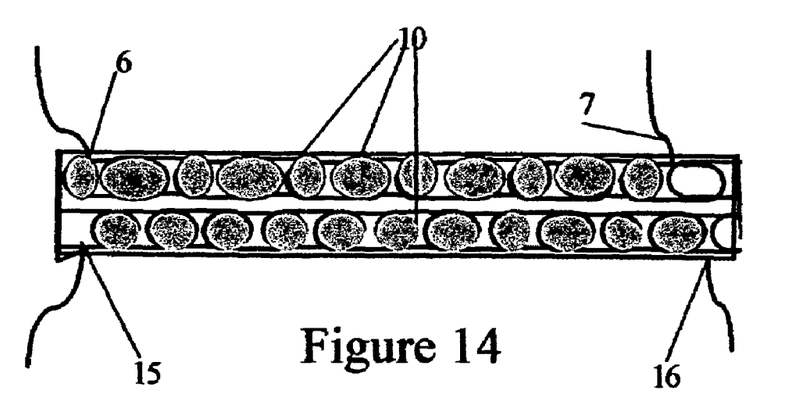
Figure 15:
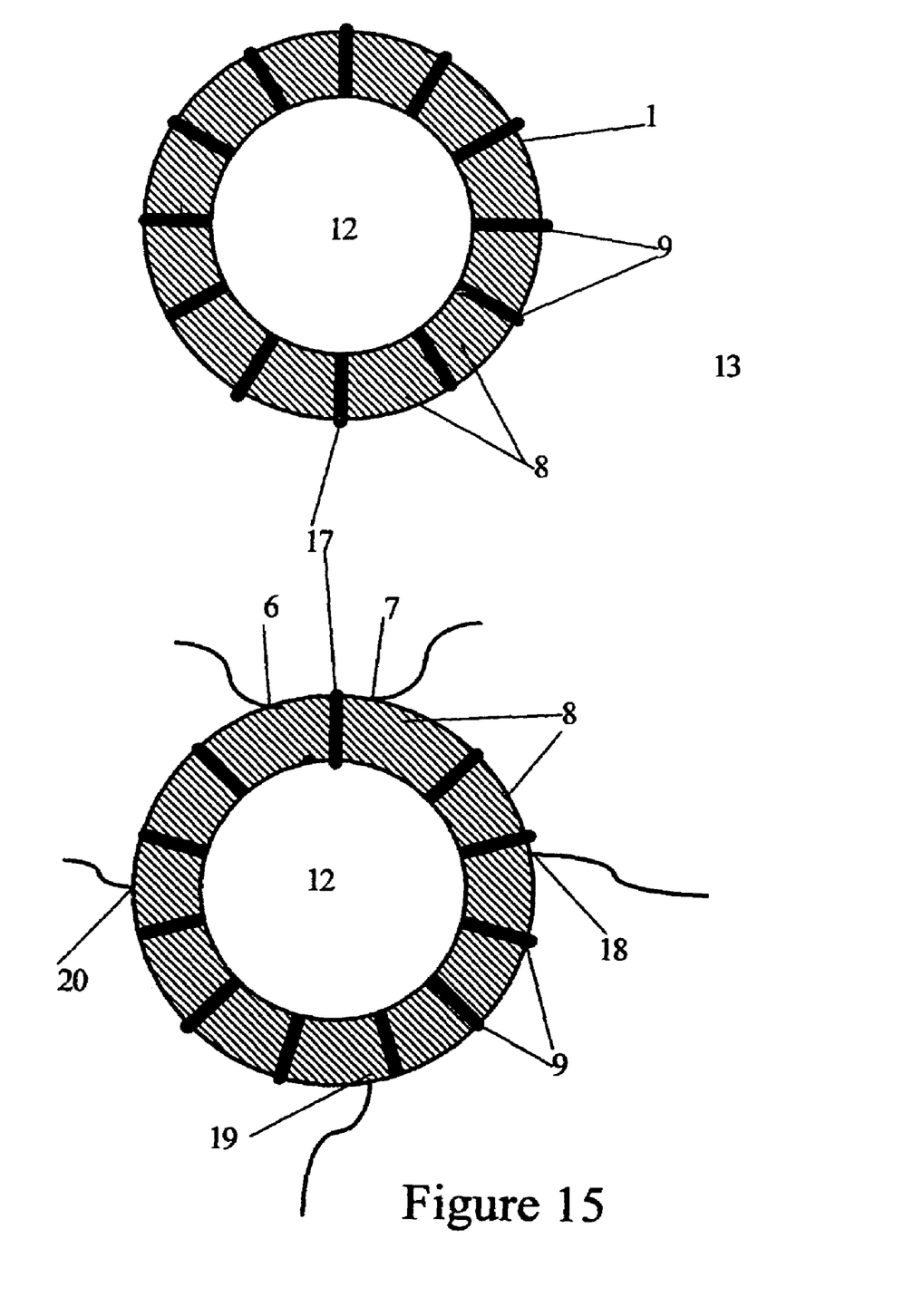
Figure 16:
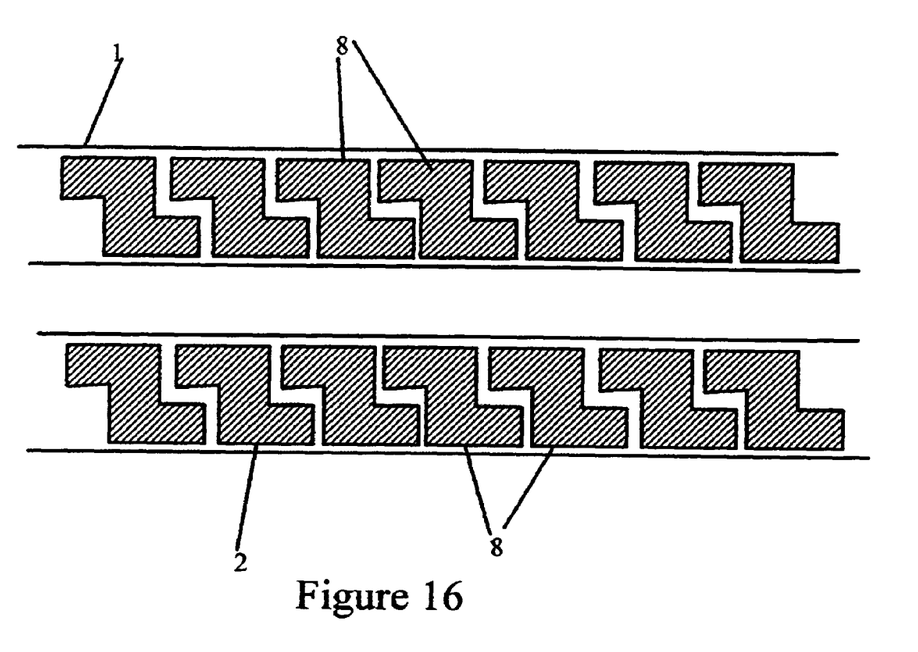
Figure 17:
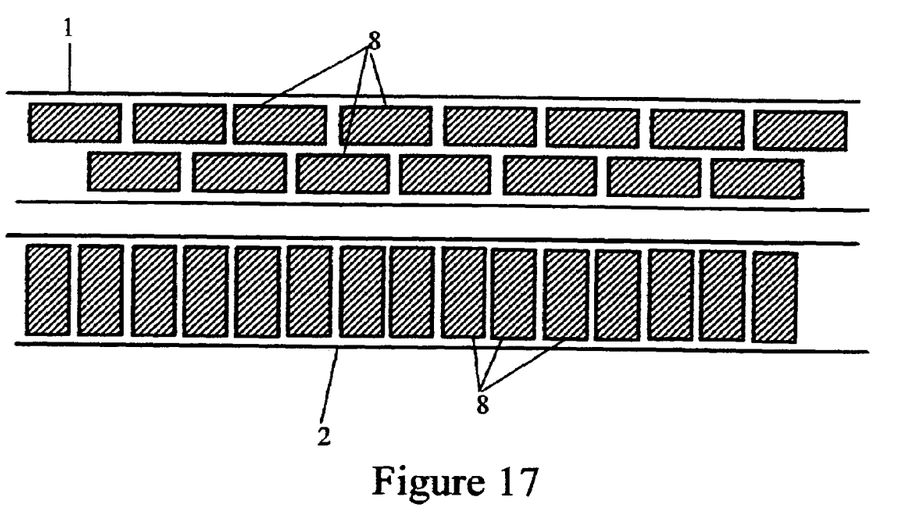
Figure 18:
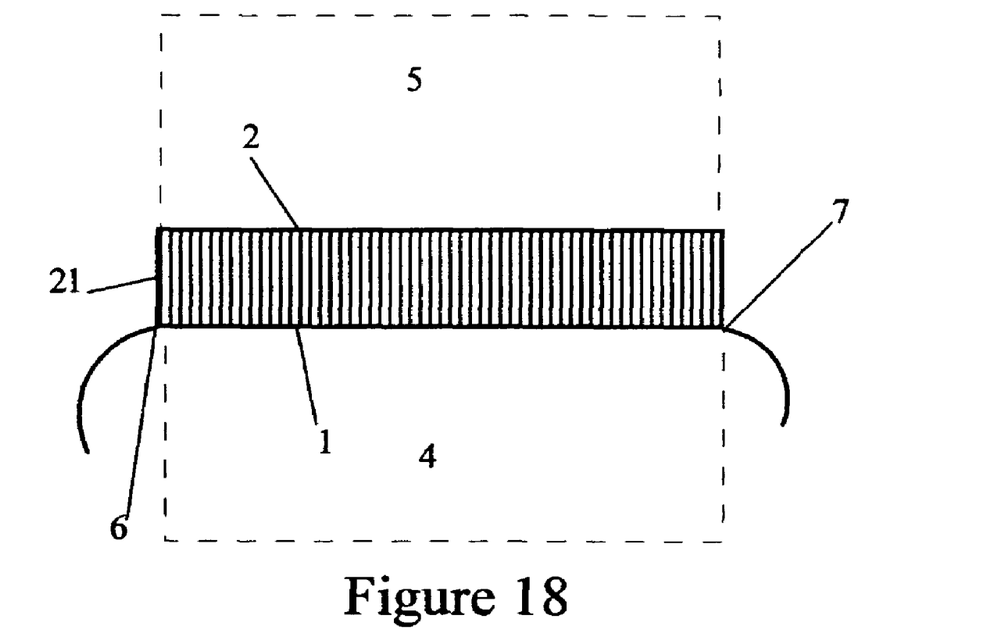
Figure 19:
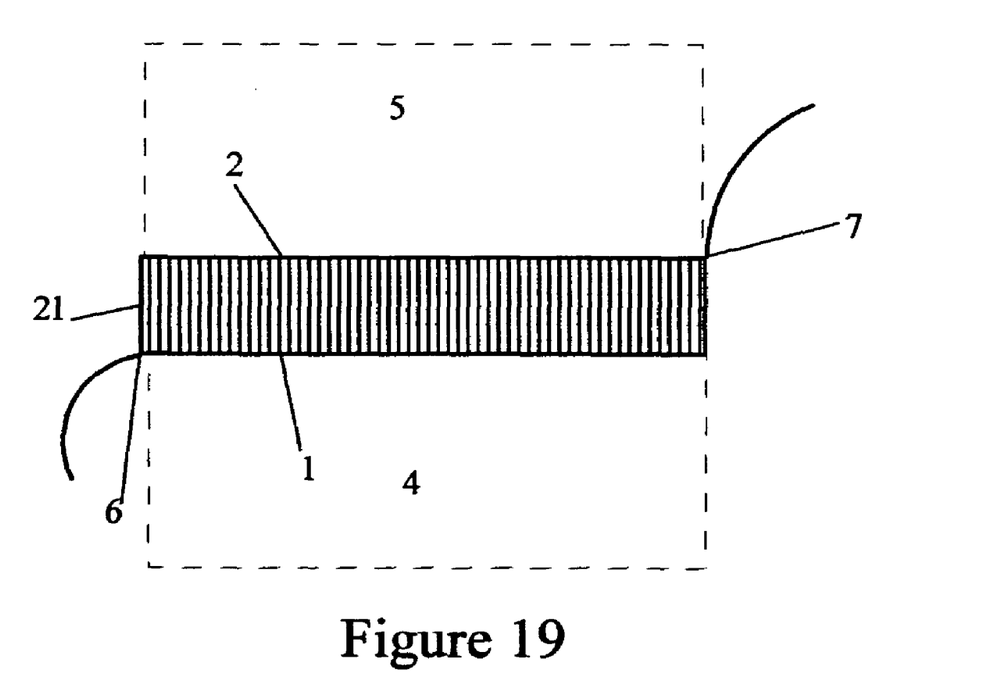

The claimed device comprises patterns that are included in the contact parts (4 and 5) and follow distortions of these parts. The way the patterns come up to each surface (1 and 2) can be different according to both the type of application and the accuracy expected in detection of detachment. At least two of the patterns are linked to electrical connection points. A device for measuring the intensity and the voltage between the connection points (6 and 7) makes it possible to measure the contact quality between the two surfaces (1 and 2) and its variations as time goes. In the event of a detachment having an effect on the conduction surface, a modification of intensity and voltage is measured between both ends of the conduction line (23). In the event of a leak or an intrusion according to a path joining the two edges of the contact surface through the conduction surface, a resistance increase or even a conduction break between the two ends of (23) is detected. As patterns (8) are positioned in series on the conduction line, the resistance variation of the conductor from end to end equals the resistance variation of one of the patterns during a contact variation between both surfaces (1 and 2). The device also works when each pattern is in contact with more than two patterns of the opposite surface. In that case, the resistance from end to end is made up of resistance in parallel and in series. In every case, the resistance variation is the result of the localized variation of the contact between both parts. The use of several connection points makes it possible to compensate for the conduction evolutions of the patterns according to outside physical parameters, temperature, pressure, by comparing the variation of resistance on each sector circumscribed by the connection points. It also makes it possible to avoid blind zones in the neighbourhood of connection points. Thus, on FIG. (15), a variation of the contact in the neighbourhood of (18) will be measured between (7) and (19). To permanently take the measurements between the pairs of connection points, we purpose to define an electric signal, preferably an alternating signal to minimize risks of electrolysis, different (in frequency or in time) for each pair of connection points.

In accordance with the objective of the present invention, the patterns(8) can be zones of strong conductivity of a seal made up of only one non homogeneous material whose resistivity evolves in a continuous way according to the conduction line or according to both the conduction line and the distance between the conduction line and a given point located in the joint volume.

In accordance with the objective of the present invention, the patterns can be zones of strong conductivity of a seal made up of several materials homogeneous or not, so that discontinuities of conductivity exist at the border between these materials.

In accordance with the objective of the present invention, it is possible to define several conductive lines on the same contact surface. This configuration makes it possible to reduce risks of leak through the insulating zone.

it is possible to position the two connection points on the ends of the contact surface, either on the same element, or one on one of the elements and the other on the other element.

it is possible to increase the number of connection points. This configuration eliminates the potential zones of non-detection in the neighbourhood of the connection points. It also makes it possible to locate the contact variations per sector. Finally, it makes it possible to correct the resistivity drift of the material following variations of physical characteristics of the environment, such as temperature, pressure.

it is possible to use a signal varying with time to do measurements. This solution reduces risks of electrolysis.

it is possible to use different signals (frequencial or temporal) to do measurements between the various connection points.

it is possible to use various kinds of patterns and in particular patterns making it possible to guarantee a contact in partial or total series between patterns of both surfaces whatever the respective position of the two surfaces, which avoids having to fit one surface to the other.

the patterns can be obtained by metallization of contact surfaces (1 and/or 2).

the patterns can be obtained by conductive polymers embedding in the parts (4 and/or 5) or any other technique making it possible to vary the electric characteristics of the material making up the two sealed parts.

The invention claimed is:

1. A device for monitoring the contact integrity between two curvilinear surfaces by measuring variations in electric resistance between connection points, said device comprising:
    a) three or more patterns distributed on each curvilinear surface; and,
    b) two or more electrical connection points,
wherein at least two of said patterns are linked to said electrical connection points, these patterns being more conductive than their surrounding and being distributed so that when the aforementioned surfaces are brought into contact, the superimposition of the patterns forms chains of conductors whose resistance increases when the contact integrity is damaged.

2. The device as claimed in claim 1, wherein the patterns are distributed on each curvilinear surface so that the superimposition of the patterns forms several independent chains of conductors when the curvilinear surfaces are brought into contact.

3. The device as claimed in anyone of claims 1 or 2, wherein the patterns are distributed on closed curvilinear surfaces so that two insulating zones of the curvilinear surfaces come in contact when the closed curvilinear surfaces are brought into contact.

4. The device as claimed in claim 1, wherein the patterns placed at each end of the chains of conductors are linked to said electrical connection points.

5. The device as claimed in claim 1, wherein many patterns are linked to said electrical connection points on each chain of conductors.

6. The device as claimed in claim 5, wherein the patterns linked to electrical connection points are positioned on only one of the contact surfaces.

7. The device as claimed in claim 1, wherein the patterns linked to electrical connection points are arbitrarily distributed between the two curvilinear surfaces.

8. The device as claimed in claims 1 or 2, wherein the patterns are obtained by metallization of the curvilinear surfaces.

9. The device as claimed in claims 1 or 2, wherein the patterns are obtained by embedding conductive polymers in the two curvilinear surfaces.

* * * * *